United States Patent [19]
Bhatnagar et al.

[11] Patent Number: 6,077,855
[45] Date of Patent: Jun. 20, 2000

[54] HEMOREGULATORY COMPOUNDS

[75] Inventors: Pradip Kumar Bhatnagar, Exton, Pa.; Michael Hartmann; Johann Hiebl, both of Linz, Austria; Peter Kremminger, Asten, Austria; Franz Rovenszky, Linz, Austria

[73] Assignees: SmithKline Beecham Corporation, Philadelphia, Pa.; Nycomed Austria GmbH, Linz, Austria

[21] Appl. No.: 09/068,489

[22] PCT Filed: Nov. 12, 1996

[86] PCT No.: PCT/US96/18344

§ 371 Date: Dec. 4, 1998

§ 102(e) Date: Dec. 4, 1998

[87] PCT Pub. No.: WO97/17959

PCT Pub. Date: May 22, 1997

Related U.S. Application Data

[60] Provisional application No. 60/006,606, Nov. 13, 1995.

[51] Int. Cl.$^7$ ............ C07D 401/02; A61K 31/44; A61K 31/40
[52] U.S. Cl. ............ 514/332; 514/252; 514/444; 544/357; 546/255; 548/518
[58] Field of Search ............ 544/357; 546/255; 548/518; 514/252, 322, 444

[56] References Cited

U.S. PATENT DOCUMENTS 4,499,081  2/1985  Laerum ..................... 514/17

FOREIGN PATENT DOCUMENTS 0 515 995  12/1992  European Pat. Off. .
6 075  6/1998  France .

OTHER PUBLICATIONS

Takemoto, et al., "Packing Materials for Liquid Chromatographic columns of Compounds Containing Nucleic Acid Bases" Jpn. Kokai Tokkyo Koho JP63 96,553, 1988 (Japan) Chemical Abstracts, vol. 111, No. 11, (1989), pp. 389–390, Abstract No. 93,482G.

Gerchakov, et al., "Quinoxaline studies. XII. N–(2–quinoxaloxyl)–alpha–amino acids", (1966), Journal of Medicinal Chemistry, vol. 9, pp. 266–268, XP002088298.
Municio et al., "Potential antitubercular compounds. III. Isonicotinoylamino acid hydrazides and hydrazones", (1961), Chemical Abstracts, vol. 55, No. 21, Abstract No. 21110a, XP002088302 & Anales Real. Soc. Espan. Fis. Y Quim., vol. 56B, (1960), pp. 303–310, & Chem. Abstracts 6th Collective Index: Formula Index, XP002088299.
Pickett, et al., "Bioinorganic Reaction Centres on Electrodes. Modified Electrodes Possessing Amino Acid, Peptide and Ferredoxin–Type Groups on a Poly(Pyrrole) Backbone", (1994), Journal of the Chemical Society, Dalton Transactions, No. 14, pp. 2181–2189, XP002066042.
Park, et al., "Oxidation of indole–3–acetic acid amino acid conjugates by horseradish peroxidase", (1987), Chemical Abstracts, vol. 107, No. 21, p. 362, Abstract No. 193893c, XP002088303 & Plant Physiology, vol. 84, No. 3, pp. 826–829 & Chemical Abstracts 12th Collective Index, XP0020088300
Saburi, et al., "Stereochemical studies of metal chelates. VIII. Absolute configuration and circular dichroism of cobalt (III) complexes with 4,7–diaza–1,10–diaminodecane (3,2,3–tet)derivatives", (1972), Chemical Abstracts, vol. 77, No. 24, Abstract No. 158116, XP002088304, & Inorg. Chim. Acta, 6(3), pp. 427–434, & Chemical Abstracts 9th Collective Index, XP002088301.

*Primary Examiner*—Zinna Northington Davis
*Attorney, Agent, or Firm*—Linda E. Hall; Stephen A. Venetianer; Charles M. Kinzig

[57] ABSTRACT

Novel compounds of the general formula (I) which have hemoregulatory activities and can be used to stimulate haematopoiesis and for the treatment of viral, fungal and bacterial infectious diseases.

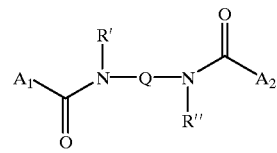

(I)

11 Claims, No Drawings

HEMOREGULATORY COMPOUNDS

This application is a 371 of PCT/US96/18344, filed Nov. 12, 1996, which claims the benefit of priority from Provisional Application No. 60/006,606, filed Nov. 12, 1995.

FIELD OF THE INVENTION

The present invention relates to novel compounds which have hemoregulatory activities and can be used to stimulate haematopoiesis and for the treatment of viral, fungal and bacterial infectious diseases.

BACKGROUND OF THE INVENTION

The haematopoietic system is a life-long cell renewal process whereby a defined stem cell population gives rise to a larger population of mature, differentiated blood cells (Dexter T M. Stem cells in normal growth and disease, Br Med J 1987; 195:1192–1194) of at least nine different cell lineages (erythrocytes, platelets, eosinophils, basophils, neutrophils, monocytes/macrophages, osteoclastes and lymphocytes) (Metcalf D. The Molecular Control of Blood Cells, 1988; Harvard University Press, Cambridge, Mass.). The stem cells are also ultimately responsible for regenerating the bone marrow following treatment with cytotoxic agents or following bone marrow transplantation.

The major dose-limiting toxicities of most standard antineoplastic drugs are related to bone marrow suppression, which if severe and prolonged, can give rise to life-threatening infectious and haemorrhagic complications. Myelosuppression is predictable and has been reported to be dose-limiting in greater than 50% of single-agent Phase I trials cytotoxic compounds (Merrouche Y, Catimel G, Clavel M. Haematopoietic growth factors and chemoprotectants; should we move toward a two-step process for phase I trials in oncology? Ann Oncol 1993; 4:471–474). The risk of infection is directly related to the degree of myelosuppression as measured by the severity and duration of neutropenia (Brody G P, Buckley M, Sathe Y S, Freireich E J. Quantitative relationship between circulating leukocytes and infections with acute leukemia. Ann In Med 1965; 64:328–334).

The control of haematopoiesis involves the interplay of a variety of cytokines and growth factors during various stages of the haematopoietic cascade, including early pluripotent stem cells and mature circulating effector cells. These regulatory molecules include granulocyte colony stimulating factor (G-CSF), granulocyte-macrophage stimulating factor (GM-CSF), macrophage-colony stimulating factor (M-CSF), and a variety of interleukines which have overlapping, additive and synergistic actions which play major roles in host defence. Mechanistically, this is accomplished by enhancing the production of granulocytes and macrophages, as well as by the activation of effector cell functions (Moore M A S. Haematopoietic growth factor interactions: in vitro and in vivo preclinical evaluation. Cancer Surveys 1990; 9:7–80). These coordinated activities support optimal host defences which are necessary for fighting bacterial, viral and fungal infections.

Strategies to prevent or reduce the severity of neutropenia and myelotoxicity include the use of haematopoietic growth factors and/or other haematopoietic cytokines. Such treatments are becoming common practice, in that they offer the potential of increased doses of cytotoxic agents that may improve the therapeutic efficacy in antineoplastic agents, and reduce the morbidity associated with their use (Steward W P. Granulocyte and granulocyte-macrophage colony stimulating factors, Lancet 1993; 342:153–157). Clinical studies have demonstrated the G-, GM- and/or M-CSF may reduce the duration of neutropenia, accelerate myeloid recovery and reduce neutropenia-associated infections and other infectious complications in patients with malignancies who are receiving cytotoxic chemotherapy or in high infectious-risk patients following bone marrow transplantation (Steward W P. Granulocyte and granulocyte-macrophage colony stimulating factors, Lancet 1993; 342:153–157 and Munn D H, Cheung N K V. Preclinical and clinical studies of macrophage colony-stimulating factor. Semin Oncol 1992; 19:395–407).

We have now found certain novel compounds which have a stimulative effect on myelopoietic cells and are useful in the treatment and prevention of viral, fungal and bacterial diseases.

SUMMARY OF THE INVENTION

This invention comprises compounds, hereinafter represented as Formula (I), which have hemoregulatory activities and can be used to stimulate haematopoiesis and in the prevention and treatment of bacterial, viral and fungal diseases.

These compounds are useful in the restoration of leukocytes in patients with lowered cell counts resulting from a variety of clinical situations, such as surgical induced myelosuppression, AIDS, ARDS, congenital myelodysplacis, bone marrow and organ transplants; in the protection of patients with leukopenia from infection; in the treatment of severely burned patients and in the amelioration of the myelosuppression observed with some cell-cycle specific antiviral agents and in the treatment of infections in patients who have had bone marrow transplants, especially those with graft versus host disease, in the treatment of tuberculosis and in the treatment of fevers of unknown origin in humans and animals. The compounds are also useful in the treatment and prevention of viral, fungal and bacterial diseases, particularly Candida, Herpes and hepatitis in both immunosuppressed and "normal" subjects.

These compounds may also be used in combination with the monomers of co-pending U.S. Application No. 07/799, 465 and U.S. Pat. No. 4,499,081, incorporated by reference herein, to provide alternating peaks of high and low activity in the bone marrow cells, thus augmenting the natural circadian rhythm of haematopoiesis. In this way, cytostatic therapy can be given at periods of low bone marrow activity, thus reducing the risk of bone marrow damage, while regeneration will be promoted by the succeeding peak of activity.

This invention is also a pharmaceutical composition, which comprises a compound of Formula (I) and a pharmaceutically acceptable carrier.

This invention further constitutes a method for stimulating the myelopoietic system of an animal, including humans, which comprises administering to an animal in need thereof, an effective amount of a compound of Formula (I).

This invention also constitutes a method for preventing and treating viral, fungal and bacterial infections in immunosuppressed and normal animals, including humans, which comprises administering to an animal in need thereof, an effective amount of a compound of Formula (I).

This invention also constitutes a method for preventing or treating sepsis in an animal which comprises administering to an animal in need thereof an effective amount of a compound of Formula (I).

DETAILED DESCRIPTION OF THE INVENTION

The compounds of the invention are represented by structural Formula I

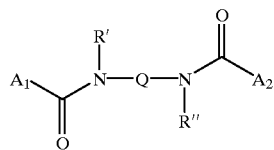

(I)

wherein:

$A_1$ equals $A_2$ and denotes a group $Z-(CH_2)k-(NR''')_q$, wherein Z is a 4–10 membered mono- or bicyclic heterocyclic ring system containing up to four heteroatoms N, O, S in the ring in which at least one heteroatom is N, and wherein the ring is substituted or unsubstituted by one or two $C_{1-4}$alkyl, F, Cl, Br, I, $C_{1-4}$ alkoxy, $(CH_2)_m R_4$, oxo, oxime, $O-C_{1-4}$alkyloxime, hydroxy, $N(R_3)_2$, acylamino or aminoacyl groups, 8, 9, 10 membered monocyclic ring systems being excluded;

R' and R'' are the same and are hydrogen, $C_{1-4}$alkylC(O)$R_4$, $C_{1-4}$alkyl or $R_1$ and $R_2$ are benzyl which is optionally substituted by one or two $C_{1-4}$alkyl, $C_{1-4}$alkoxy, F, Cl, I, Br, OH, or $N(R_3)_2$;

k is an integer from 0 to 4;

R''' denotes Hydrogen, $C_{1-4}$-alkyl or $C_{1-4}$-alkylcarboxylic acid;

q is an integer from 0 to 1;

Q denotes a group

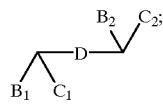

wherein:

$B_1$ equals $B_2$ and denotes halogen, $-(CH_2)_m-CN$, $-(CH_2)_{m+1}-R^2$, $-(CH_2)_m-R^3$, $-(CH_2)_m-COR^2$ or $-(CH_2)_m-COR^3$; where $R^2$ denotes $-OR^3$, $-NR^3_2$, $-SR^3$; and $R^3$ is independently hydrogen, $C_1-C_4$-alkyl or benzyl; and m is an integer from 0 to 4;

$C_1$ equals $C_2$ and denotes halogen, $-(CH_2)_n-CN$, $-(CH_2)_{n+1}-R^4$, $-(CH_2)_n-R^3$, $-(CH_2)_n-COR^4$ or $-(CH_2)_n-COR^5$; where $R^4$ is independently $-OR^3$, $-NR^3_2$, $-SR^3$; and n is an integer from 0 to 4; and D denotes $-(CH_2)_x-E-(CH_2)_y-$; wherein E denotes a single bond or $-C=C-$, $-C\equiv C-$, or $-NH-$, $-O-$,

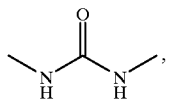

$-S-$ or $-S-S-$; and x and y independently denote an integer from 0 to 5; with the proviso that x and y are not 0 if E denotes $-NH-$, $-O-$, $-S-$ or $-S-S-$;

and with the proviso that $B_1$ is not identical to $C_1$ and $B_2$ is not identical to $C_2$, and pharmaceutically acceptable salts thereof.

Z in the above Formula (I) denotes an optionally substituted pyrrolyl, isopyrrolyl, pyrazolyl, isoimidazolyl, triazolyl, isoxazolyl, oxazolyl, thiazolyl, isothiazolyl, oxadiazolyl, pyridinyl, pyridazinyl, pyrimidinyl, pyrazinyl, pyrrolidinyl, piperazinyl, triazinyl, morpholinyl, indolyl, indoleninyl, isobenzazolyl, pyrindinyl, isoindazolyl, indoxazinyl, benzoxazolyl, quinolinyl, isoquinolinyl, cinnolinyl, quinazolinyl, naphthyridinyl, pyridopyridinyl, tetrahydroquinolinyl, tetrahydroisoquinolinyl, quinoxalinyl, indolinyl, pyrrolidonyl, imidazolyl, imidazolidinyl, imidazolinyl, piperidyl, tetrazolyl, quinuclidinyl, azetidinyl, or purinyl;

Preferred compounds are those wherein Z is optionally substituted pyridinyl, pyrimidinyl, pyrazinyl, pyridazinyl, quinolinyl, tetrahydroquinolinyl, azetidinyl, or pyrrolidinyl.

More preferred compounds are those wherein Z is optionally substituted 2-pyridinyl, 2-pyrimidinyl, 2-pyrazinyl, 2-pyrrolidon-5-yl, or 2-pyrrolidinyl.

Possible substituents for Z are $C_{1-4}$-alkyl, $C_{1-4}$-alkoxy, $C_{1-4}$-alkoxy-$C_{1-4}$-alkyl, oxo, oxime, $O-C_{1-4}$-alkyloxime, hydroxy, amino, $C_{1-4}$-alkylamino, di-$C_{1-4}$-alkylamino, acylamino and aminoacyl.

Preferred substituents for Z are methyl, ethyl, methoxy, methoxymethyl, oxo, oxime, hydroxy, amino, ethylamino or dimethylamino.

Preferred groups R' and R'' are hydrogen, methyl and ethyl.

Alkyl groups may be straight or branched.

The compounds of the present invention may contain one ore more asymmetric carbon atoms and may exiwst in racemic and optically active forms. All the compounds and diastereomers are contemplated to be within the scope of the present compounds.

Especially preferred compounds are:

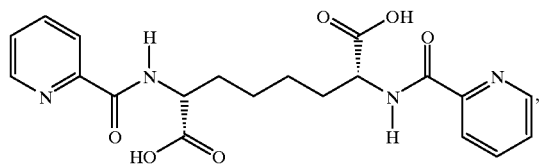

and

-continued

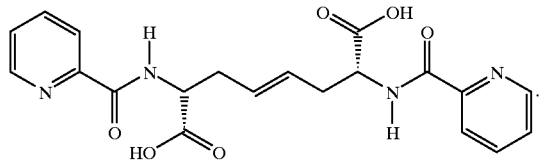
5

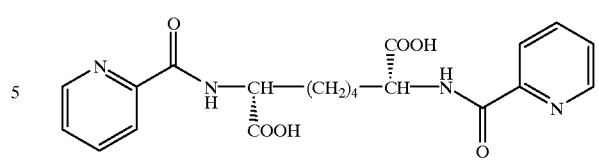
6 a) e⁻, pyridine, methanol; b) 4N HCl/dioxane; c) EDC, DMF;
d) $H_2$, 10% Pd/C, methanol Methods Of Preparation Compounds of Formula (I) wherein E is a single bond; and R', R", R''', $C_1$, $C_2$, $B_1$, $B_2$, $A_1$, $A_2$, Z, k, m, n, x and y are defined as in Formula (I) are prepared by methods analogous to those described in Scheme 1.

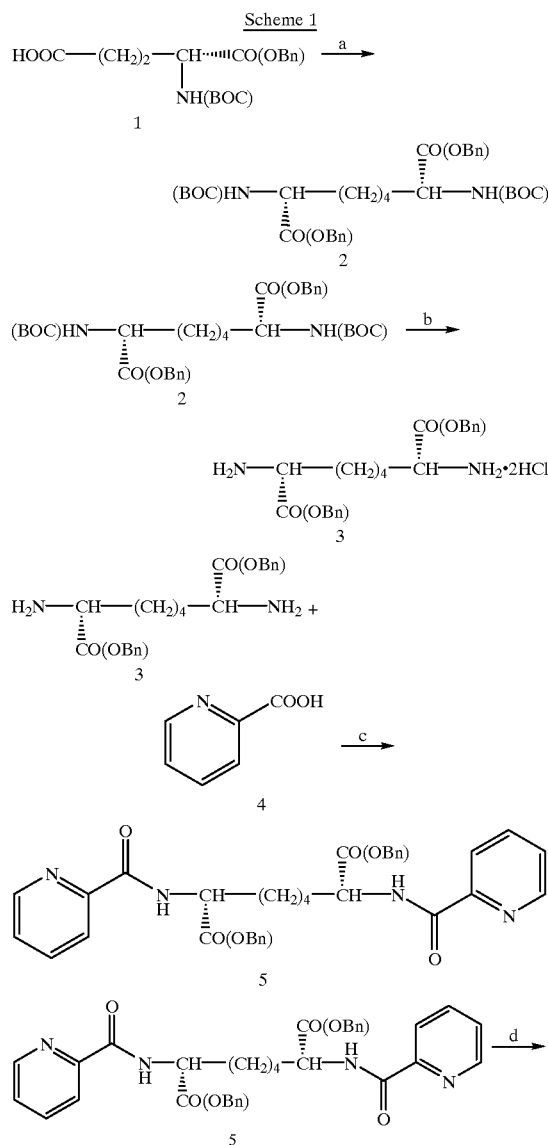

Two suitably protected amino acids, such as 1 in Scheme 1, are coupled, using electrochemical methods in an appropriate solvent (such as pyridine/methanol). Removal of the amino-protecting group of 2 in Scheme 1 under standard acidic conditions (such as 4N HCl/dioxane) is followed by acylation of the resulting hydrochloride with appropriate heterocyclic acids, such as 4 in Scheme 1, using an activating agent such as EDC in a suitable aprotic polar solvent (such as DMF). Subsequent removal of the remaining protecting group using hydrogen and an appropriate catalyst (such as 10% Pd/C) in a suitable solvent (such as methanol) furnishes the product 6 in Scheme 1.

Compounds of Formula (I) wherein E, R', R", R''', $C_1$, $C_2$, $B_1$, $B_2$, $A_1$, $A_2$, Z, k, m, n, x and y are defined as in Formula (I) are prepared by methods analogous to those described in Scheme 2.

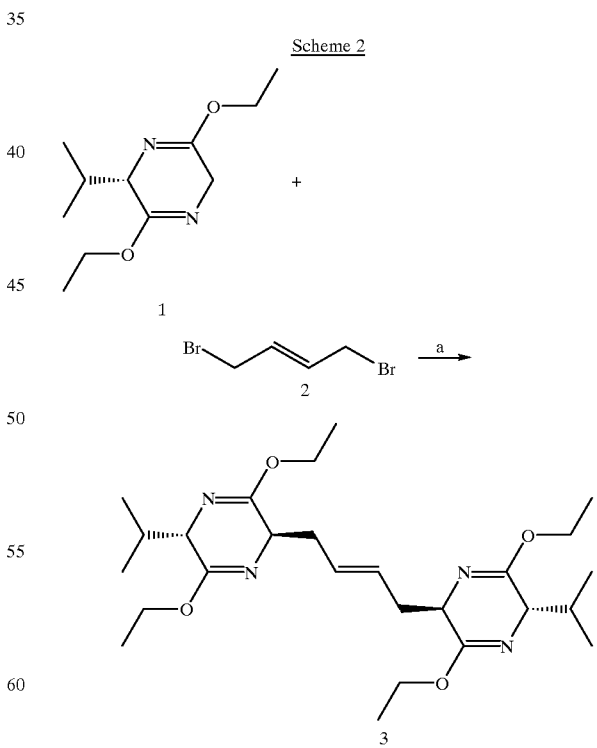

-continued

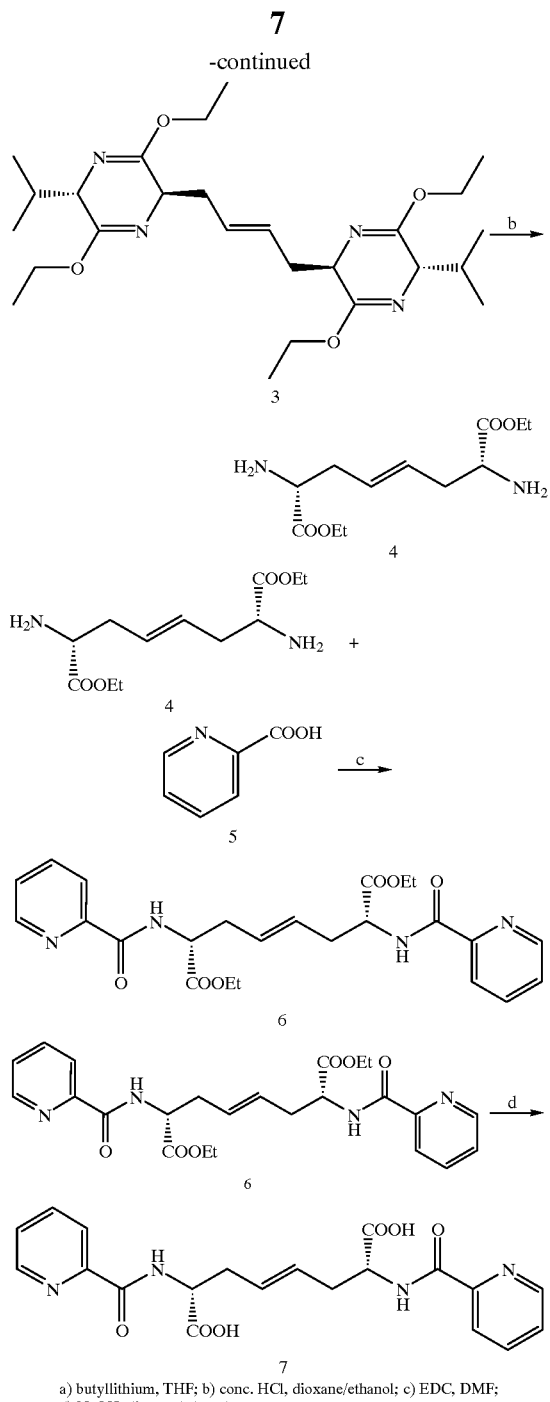

a) butyllithium, THF; b) conc. HCl, dioxane/ethanol; c) EDC, DMF;
d) NaOH, dioxane/ethanol (2S)-2,5-Dihydro-3,6-diethoxyisopropylpyrazine (1 in Scheme 2) is coupled with an appropriate dielectrophile, such as 2 in Scheme 2, using a strong base (such as butyllithium) in a suitable solvent (such as THF) to give 3 in Scheme 2. Hydrolysis and ring-opening under standard acidic conditions (such as diluted HCl) in a suitable solvent (such as dioxane/ethanol) leads to a diamine, such as 4 in Scheme 2, which is then bis-acylated with appropriate heterocyclic acids, such as 5 in Scheme 2, using an activating agent (such as EDC) in an aprotic polar solvent (such as DMF). Hydrolysis of the ester under standard basic conditions (such as NaOH) in a suitable solvent (such as dioxane/ethanol) furnishes the product 7 in Scheme 2.

In order to use a compound of the Formula (I) or a pharmaceutically acceptable salt thereof for the treatment of humans and other mammals it is normally formulated in accordance with pharmaceutical practice as a pharmaceutical composition.

According to a still further feature of the present invention there are provided pharmaceutical compositions comprising as active ingredient one or more compounds of Formula (I) as herein before defined or physiologically compatible salts thereof, in association with a pharmaceutical carrier or excipient. The compositions according to the invention may be presented for example, in a form suitable for oral, nasal, parenteral or rectal administration.

As used herein, the term "pharmaceutical" includes veterinary applications of the invention. These peptides may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline and water. Solid carriers include starch, lactose, calcium sulfate dihydrate, terra alba, magnesium stearate or stearic acid, talc, pectin, acacia, agar or gelatin. The carrier may also include a sustained release material such as glyceryl monostearate or glyceryl distearate, alone or with a wax. The amount of solid carrier varies, but, preferably will be between about 20 mg to about 1 g per dosage unit. The pharmaceutical preparations are made following the conventional techniques of pharmacy involving milling, mixing and filling for hard gelatin capsule forms. Capsules containing one or several active ingredients may be produced, for example, by mixing the active ingredients with inert carriers, such as lactose or sorbitol, and filling the mixture into gelatin capsules. Organ specific carrier systems may also be used.

Alternately pharmaceutical compositions of the peptides of this invention or derivatives thereof, may be formulated as solutions of lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration and contained in a metered dose inhaler or nebulizer for insufflation. It may be desirable to add excipients such as polyvinylpyrrolidone, gelatin, hydroxycellulose, acacia, polyethylene glycol, mannitol, sodium chloride or sodium citrate.

For rectal administration, a pulverized powder of the peptides of this invention may be combined with excipients such as cocoa butter, glycerin, gelatin or polyethylene glycols and molded into a suppository. The pulverized powders may also be compounded with oily preparation, gel, cream or emulsion, buffered or unbuffered, and administered through a transdermal patch.

Nasal sprays may be formulated similarly in aqueous solution and packed into spray containers either with an aerosol propellant or provided with means for manual compression.

Dosage units containing the compounds of this invention preferably contain 0.05–50 mg, for example 0.05–5 mg of the compound of Formula (I) or of the salt thereof.

According to a still further feature of the present invention there is provided a method of stimulation of myelopoiesis which comprises administering an effective amount of a pharmaceutical composition as hereinbefore defined to a subject.

No unacceptable toxicological effects are expected when compounds of the invention are administered in accordance with the present invention.

The biological activity of the compounds of Formula (I) is demonstrated by the following tests.

Induction of Hematopoietic Synergistic Activity in Stromal Cells

The murine bone marrow derived from stromal cell line C6.4 is grown in 12 well pates in RPMI 1640 with 10% FBS. Upon reaching confluence, the C6.4 cells are washed and the media exchanged with fresh RPMI 1640 without FBS. Confluent cell layers of murine C6.4 cells are treated with compound. Cell free supernatants are collected 18 hours later. Supernatants are fractionated with a Centricon-30 molecular weight cut-off membrane. C6.4 cell hematopoietic synergistic factor (HSF) activity is measured in a murine CFU-C assay.

CFU-C Assay

Bone marrow cells are obtained from C57B1/6 female mice and suspended in RPMI 1640 with 10% FBS. Bone marrow cells (7.5E+4 cells/mL) are cultured with sub optimal levels of CFU plus dilutions of test C6.4 cell 30K-E supernatants from above in a standard murine soft agar CFU-C assay. Cell aggregates >50 cells are counted as colonies. The number of agar colonies counted is proportional to the amount of HSF present within the C6.4 bone marrow stromal line supernatant.

Effector Cell Function Assay

Female C57B1 mice are administered test compound PO daily for 8 days. Resident peritoneal exudate cells (PEC) utilized ex vivo from treated or untreated mice are harvested with cold calcium and magnesium-free DPBS supplemented with heparin and antibiotics within 2–4 hours following the last injection. Adherent PEM populations are prepared by incubating standardized PEC suspensions in microtiter dishes for 2 hours at 37° C. (5% $CO_2$) and removing nonadherent cells by washing the wells with warm buffer.

The superoxide dismutase-inhibitable (SOD) superoxide released by effector cells in response to a in vitro stimulation by phorbol myristate acetate (PMA) (100–200 nM) or pre-opsonized (autologous sera) live C. albicans (E:T=1:10) are quantitated in a microtiter ferricytochrome c reduction assay. The assay is performed in the presence of 1% gelatin/HBSS and 80 $\mu M$ ferricytochrome c in a total volume of 200 $\mu L$/well. The nmoles of cytochrome c reduced/well is calculated from spectrophotometric readings (550 nm) taken following a 1 hour incubation at 37° C. (5% $CO_2$). The amount of SOD-inhibitable cytochrome c reduced is determined by the inclusion of wells containing SOD (200 U/well). Baseline superoxide release is determined in the absence of stimuli. Experimental data are expressed as a percentage of the control group.

EXAMPLE 1

(R,R)-2,7-Bis-(2-pyridylcarbonylamino)-octanoic-(1,8)-diacid

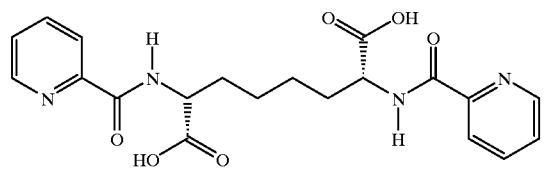

Preparation of (R,R)-2,7-Bis-(t-butyloxycarbonylamino)-octanoic-(1,8)-diacid-dibenzylic-ester

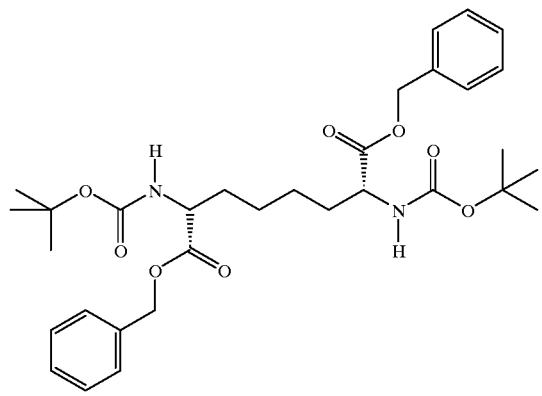

Boc-D-glutamic acid a-benzyl ester (Boc-D-Glu-OBn, 60 g, 178 mmol) is dissolved in a 3:1 mixture of methanol : pyridine (240 ml). The solution is transferred to an electrolysis cell equipped with a cooling jacket and Pt electrodes. A methanolic solution of sodium methoxide (30% w/w, 0.5 ml) in methanol is added and the electric current passed (5 amp at 50–80 Volts) through the cell keeping the temperature between 18 to 25° C. by cooling with a cryostat. The reaction is sampled periodically (TLC: ethyl acetate-:petroleum ether=1:4) and once all the starting material is consumed the electrolysis is stopped. The solution is concentrated at reduced pressure and chromatographed over silica gel using ethyl acetate:petroleum ether=1:4 as eluent to yield after crystallisation from cyclohexane:n-hexane (1:1) solvent mixture (R,R)-2,7-Bis-(t-butyloxycarbonylamino)-octanoic-(1,8)-diacid-dibenzylic-ester (13.0 g, 25%), mp. 107–110° C.

Preparation of (R,R)-2,7-diamino-octanoic-(1,8)-diacid-dibenzylic-ester

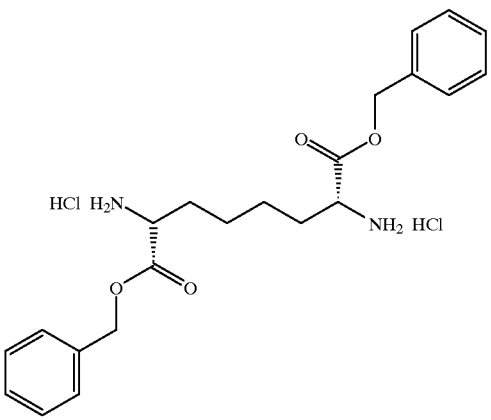

To a solution of (R,R)-2,7-Bis-(t-butyloxycarbonylamino)-octanoic-(1,8)-diacid-dibenzylicester (7.02 g, 12 mmol) in dry dioxane a 5.9 M HCl in dioxane (24 ml) was added. The mixture was stirred at r.t. for 1 h under a $N_2$-atmophere. After 15 min a white precipitate formed. The volatile compounds were removed at reduced pressure. The white residue was digerated with dry dioxane (20 ml) and the solvent was removed under reduced pressure. The resulting precipitate was washed with dry diethyl ether (3×30 mL), carefully separated and dried in high vacuum yielding quantitatively the hydrochloride salt of (R,R)-2,7-diamino-octanoic-(1,8)-diacid-dibenzylic-ester.
Preparation of (R,R)-2,7-Bis-(2-pyridylcarbonylamino)-octanoic-(1,8)-diacid-dibenzylic-ester

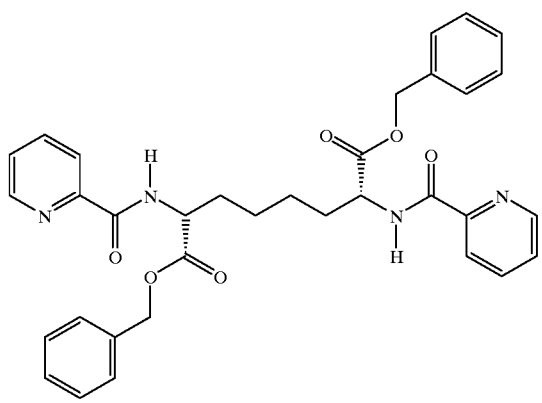

To a stirred solution of (R,R)-2,7-diamino-octanoic-(1,8)-diacid-dibenzylic-ester (3.69 g, 8 mmol) in dry DMF (23 ml) picolinic acid (1.97 g, 16 mmol), diisopropylethylamine (2.74 ml, 16 mmol), HOBt (3.68 g, 16 mmol) and EDC (4.59 g, 16 mmol) each dissolved in DMF (2 ml each) was added in this order at 0° C. under a $N_2$ atmosphere. After 1 h the mixture was allowed to come to r.t. and stirred for further 1.5 h. The reaction was quenched by pouring it on a cooled (0° C.) mixture of saturated aqueous $NaHCO_3$ solution (170 ml) and water (70 ml), whereupon a yellow oil separated. The whole mixture was extracted with $CHCl_3$ (3×60 ml). The combined organic layer was exhaustively washed with water (6×60 ml), separated, dried over $Na_2SO_4$ and concentrated under reduced pressure. The residue was recristallized from methanol (8 ml) to yield (R,R)-2,7-Bis-(2-pyridylcarbonylamino)-octanoic-(1,8)-diacid-dibenzylic-ester (2.81 g, 59%).

m.p.: 85–86° C.

Preparation of (R,R)-2,7-Bis-(2-pyridylcarbonylamino)-octanoic-(1.8)-diacid

To a solution of (R,R)-2,7-Bis-(2-pyridylcarbonylamino)-octanoic-(1,8)-diacid-dibenzylic-ester (3.3 g, 5.55 mmol) in MeOH (120 ml) 10% Pd/C (500 mg) was added and the mixture was shaken for 1 h under a hydrogen atmosphere (1 bar) in a Parr apparatus. The catalyst was removed by filtration and the solvent of the effluent was removed under reeduced pressure. The slightly yellow residue was crystallized from $CH_3CN$ (40 ml) to yield (R,R)-2,7-Bis-(2-pyridylcarbonylamino)-octanoic-(1,8)-diacid (2.12 g, 92%).

m.p.: 85–87° C.

$^1H$ NMR (400 MHz, $d_4$-MeOH) d 1.50–1.60 (m, 4 H), 1.91–1.98 (m, 2 H), 2.02–2.11 (m, 2 H), 4.66 (dd, 2 H, J=5.0, 8.0 Hz), 7.59 (ddd, 2 H, 1.4, 4.9, 7.8 Hz), 7.98 (dt, 2H, J=1.6, 7.8Hz),8.1 (dt,2 H, J=1.1, 7.8 Hz), 8.67(dt, 1 H, J=1.1, 4..9 Hz);

$^{13}C$ NMR(100 MHz, $d_4$-MeOH) d 175.3, 166.7, 150.9, 150.1, 139.1, 128.2, 123.5, 54.0, 33.12, 26.64;

ES MS m/z 415.4 (M+H$^+$);

EXAMPLE2

(R,R)-2,7-Bis-(2-pyridylcarbonylamino)-decanoic-(1,8)-diacid

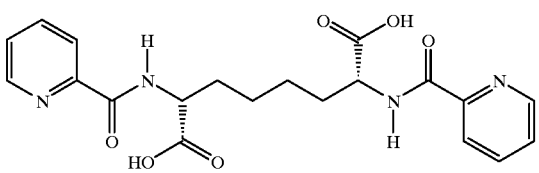

Preparation of 1,6-Bis-((2S,5R)-2,5-dihydro-3,6-diethoxy-2-isopropyl-5-pyrazinyl)-hexane

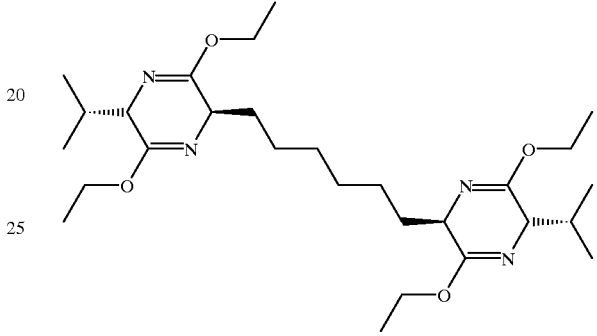

(2S)-2,5-Dihydro-3,6-diethoxyisopropylpyrazine (2.03 g; 9.6 mmol) was dissolved in THF (150 ml) and a 1.6 M solution of butyllithium in hexane was added at −78° C. (6.0 ml; 80.2 mmol). After 1 h at −78° C. a solution of the dielectrophile (1,6-dibromohexane (2.3 g, 9.6 mmol)) in 30 ml THF was added dropwise and the mixture was allowed to come to room temperature overnight. After hydrolysis of the mixture by pouring it on a 1 M phosphate buffer solution (240 ml, pH 7.2), the mixture was extracted with diethyl ether (3×200 ml) and the combined organic layers were dried over $MgSO_4$. After filtration and drying ($Na_2SO_4$), the solvents were removed on the rotary evaporator and the residue was dried under vacuum. The crude product was purified by flash chromatography petrol ether/ethyl acetate 9/0.5 to yield 13.4% of an oily product. The purity and diastereomeric excess was determined by capillary GC.

Preparation of (R,R)-2,9-diaminodecane-1,10-diacid-diethylester

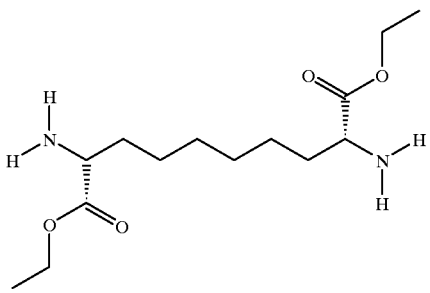

1,6-Bis-((2S,5R)-2,5-dihydro-3,6-diethoxy -2-isopropyl-5-pyrazinyl)-hexane (0.50 g; 0.98 mmol) was dissolved in dioxane (80 ml) and EtOH (160 ml) and a solution of conc. HCl (6.25 ml, 75.0 mmol) in water (160 ml) was added dropwise. The mixture was stirred overnight and the organic solvents were stripped off. A conc. aqueous ammonia solution was added until a pH of 9 was reached and the aqueous layer was extracted with chloroform (3×80 ml). The combined organic layers were dried (MgSO$_4$), filtered and the solvent was removed. Remaining ValOEt was removed by Kugelrohr distillation (room temperature, 0.05 Torr) to yield (R,R)-2,9-diaminodecane-1,10-diacid-diethylester (0.17 g, 61%) as a pale yellow oil.

Preparation of (R,R)-2,9-bis-(2-pyridylcarbonylamino)-decanoic-(1,10)-diacid-diethylester

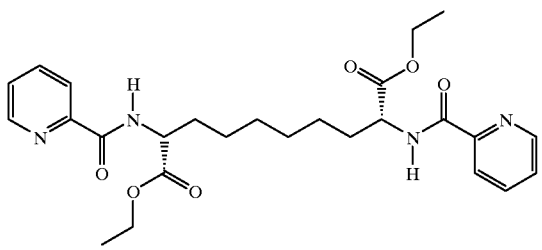

Picolinic acid (0.15 g; 1.21 mmol) was suspended in 100 ml dichloromethane and a solution of (R,R)-2,9-diaminodecane-1,10-diacid-diethylester (0.17 g, 0.59 mmol) was added. The clear solution was cooled to 0° C. and HOBt (6.36 g, 40 mmol) and DCC (7.68 g, 37.3 mmol) were added. The reaction mixture came to room temperature overnight and was extracted with 4% NaHCO$_3$ solution. The combined organic layers were dried over MgSO$_4$, filtered and the solvent was removed. The residue was purified by flash chromatography (silica gel; petrol ether/ethyl acetate 1/1) to yield (R,R)-2,9-bis-(2-pyridylcarbonylamino)-decanoic-(1,10)-diacid-diethylester as semicrystalline compound (0.30 g, 100%).

Preparation of (R,R)-2,7-bis-(2-pyridylcarbonylamino)-decanoic-(1,8)-diacid

To a cooled (0° C.) solution of (R,R)-2,9-bis-(2-pyridylcarbonylamino)-decanoic-(1,10)-diacid-diethylester (0.30 g, 0.60 mmol) in dioxane (4 ml) and EtOH (4 ml) an aqueous 2N NaOH solution (4 ml, 8.0 mmol) and water (2 ml) was added. The mixture was allowed to come to r.t. overnight. The solution was concentrated to approximately 5 ml under reduced pressure and the pH of the residual solution was adjusted to pH 3 by addition of aqueous 4N HCl, whereupon an oil separated. The mixture was extracted with ethyl acetate (3×15 ml). The combined organic layer was dried (MgSO$_4$), concentrated and the residue purified by flash chromatography (chloroform/MeOH/HOAc 8/1/1) to yield (R,R)-2,7-bis-(2-pyridylcarbonylamino)-decanoic-(1,8)-diacid (0.24 g, 82%).

$^1$H NMR (400 MHz, d$_6$-DMSO) d 8.65 (m, 4 H), 8.01 (m, 4 H), 7.6 0(m, 2 H), 4.40 (m, 2 H), 1.83 (m, 4 H), 1.26 (m, 8 H);

$^{13}$C NMR (100 MHz, d$_6$-DMSO): d 173.5, 163.5, 149.5, 148.6, 138.0, 126.8, 121.9, 52.3, 31.3, 28.6, 25.3;

The following compounds were prepared in an analogous manner to the above described examples:

EXAMPLE 3

(S,S)-2,5-Bis-(2-pyridylcarbonylamino)-hexanoic-1,6-diacid

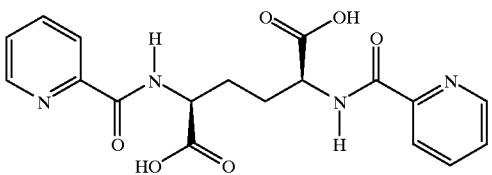

$^1$H NMR (d$_4$-MeOH, 400 MHz) d 2.01(m, 2 H, CH$_2$), 2.20 (m, 2 H, CH$_2$), 4.65 (br s, 2 H, 2 CH), 7.56 (dd, 2 H, J=4.7, 7.0 Hz, picolyl-H), 7.94 (t, 2 H, J=6.8 Hz, picolyl-H), 8.07 (d, 2 H, J=7.7 Hz, picolyl-H), 8.65 (br s, 2 H, picolyl-H);

$^{13}$C NMR (d$_4$-MeOH, 100 MHz) d 30.0 (2 CH$_2$), 54.8 (2 CH), 123.4, 128.1, 139.0, 150.0, 151.0, 166.5, 176.2;

EXAMPLE 4

(R,R)-2,5-Bis-(2-pyridylcarbonylamino)-hexane-1,6-diol

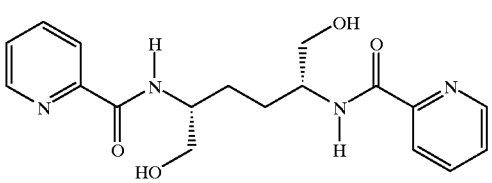

(R,R)-2,5-diamino-hexanoic-(1,6)-diacid-dibenzylic-ester (0.83 g, 1.47 mmol) was dissolved in THF (10 ml) and LiBH$_4$ (70 mg, 3.28 mmol) was added under an inert atmosphere. The suspension was stirred overnight at room temperature. After TLC control (RP-18, CH$_3$CN:H$_2$O=3:2) the reaction was poured into 100 ml of a 1% KHSO$_4$-solution and stirred for 30 min. The aqueous phase was extracted with CHCl$_3$ (3'100 ml). The combined organic phases were dried with NaSO$_4$, filtered and concentrated in vacuo. The crude product was chromatographiedover RP-18 using CH$_3$CN:H$_2$O=3:2 as eluent to yield 0.47 g (89.5%) as an oil.

$^1$H NMR (CDCl$_3$, 400 MHz) d 1.75 (m, 2 H, CH$_2$), 1.83 (m, 2 H, CH$_2$), 3.65 (br s, 2 H, D$_2$O-exchangeable, 2 OH), 3.75 (d, 4 H, J=4.4 Hz, 2 CH$_2$OH), 4.20 (m, 2 H, 2 CH), 7.35 (ddd, 2 H, J=1.2, 4.8, 7.7 Hz, 2 picolyl-H), 7.78 (dt, 2 H, J=1,6, 7.6Hz, 2 picolyl-H), 8.11 (d, 2 H, J=7.8 Hz, 2 picolyl-H), 8.23 (d, 2 H, J=8.8 Hz, NH), 8.47 (br d, 2 H, J=4.7 Hz, 2 picolyl-H).

$^{13}$C NMR (CDCl$_3$,100 MHz) d 27.9 (2 CH$_2$), 51.6 (2 CH), 64.8 (2 CH$_2$OH), 122.3, 126.162 137.3, 148.1, 149.7, 164.8;

EXAMPLE 5

(R,R)-2,7-Bis-((2S)-5-oxo-2-pyrrolidylcarbonylamino)-octanoic-1,8-diacid

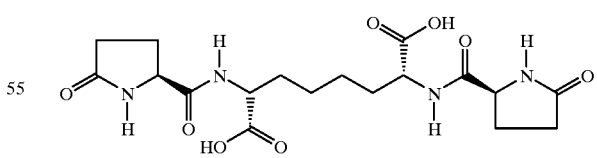

$^1$H NMR (400 MHz, D$_2$O) d 1.30–1.37 (m, 0.63–1.87 (m, 4 H), 1.98–2.08 (m, 2 H), 2.37–2.58 (m, 6 H), 4.16 (dd, 2 H, J=4.7, 9.2 Hz), 4.35 (dd, 2 H, J=5.8, 9.0);

$^{13}$C NMR (100 MHz, D$_2$O) d 27.4, 28.0, 32.1, 33.8, 57.5, 59.7, 176.8, 181.2, 184.9;

EXAMPLE 6

(R,R)-2,7-Bis-(2,pridylcarbonylamnino)-(E)-oct4-enoic-1,8-diacid-diethylester

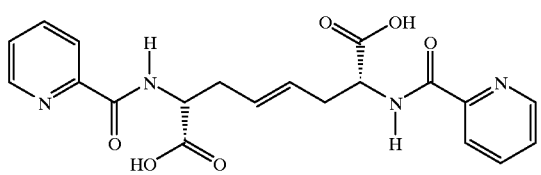

$^1$H NMR (400 MHz, $d_6$-DMSO) d 8.61 (m, 4 H), 7.97 (m, 4 H), 7.58 (m, 2 H), 5.52 (t, 2H, J=3.5 Hz), 4.44 (m, 2 H), 2.57 (m, 4 H);

$^{13}$C NMR (100 MHz, $d_6$-DMSO) d 172.7, 163.6, 149.3, 148.6, 138.0, 128.7, 126.9, 121.9, 52.1, 34.2;

EXAMPLE 7
N,N'-Bis-picolyl-D,D-cystine dimethylester (H-D-Cys-OMe)2.2 HCl (1.0 g, 2.93 mmol; obtained from Bachem) was dissolved in DMF (10 mL) and picolinic acid (0.79 g, 6.45 mmol) and DIEA (1.05 mL, 6.153 mmol) were added and the solution cooled to minus 25° C. HOBt (0.99 g, 6.45 mmol) and WSC (1.24 g, 6.45 mmol) were added. The reaction was stirred for 1 hour at 25° C. and then 1 h at ambient temperature. The resulting yellow solution as poured into water (150 mL) containing NaHCO3 (12 g) and stirred for 5 min. The resulting emulsion was extracted with ethyl acetate (2×100 mL). The combined organic phases were washed with a 5% $KHSO_4$ solution followed by deionized water until neutral. The organic phase was dried with $Na_2SO_4$, filtered, and concentrated. The residue was purified by chromatography (silica gel, eluent: petroleum ether/ethyl acetate=1/1) yielding 1.37 g (97.9%) of the title compound as an oil.

MW 478.549

Anal: (C20H22N4O6S2) Calc: C 50.20, H 4.63, N 11.71 found C 49.8, H 4.6, N 11.5.

EXAMPLE 8
N,N-Bis-picolyl-D,D-cystine

The compound of Example 7, (1.23 g, 2,57 mmol) was dissolved in MeOH (20 mL) containing water (4.6 mL). LiOH (3.73 mL of a 2N solution) was added. The resulting yellow solution was stirred for 45 min at ambient temperature. Then the solution was concentrated (removing of MeOH) and addition 5 mL of water were added. The solution was acidified with 5% $KHSO_4$ solution (13 mL) and the aqueous solution was extracted with ethyl acetate (2×50 mL) and $CH_2Cl_2$ (1×50 mL). The combined organic phases were dried with $Na_2SO_4$, filtered, and concentrated. The resulting residue was purified by chromatography (silica RP-18, eluent: MeOH/Water=½) yielding 150 mg (13%) of very pure title compound as a foam.

MW 450.495

Anal: (C18H18N4O6S2) Calc: C47.99, H 4.03, N 12.44 found C47.5, H 4.4, N 12.1.

EXAMPLE 9
N,N'-Bis-picolyl-L,L-cystine dimethylester the title compound was prepared from (H—L—Cys—OMe)2.2HCl (obtained from Bachem) as described for Example 7. Yield: 1.30 g (92.9%), oil

MW 478.549

Anal: (C20H22N4O6S2) Calc: C 50.20, H 4.63, N 11.71 found C 49.8, H 4.8, N 11.6.

EXAMPLE 10
N,N'-Bis-picolyl-L,L-cystine

The title compound was prepared using the compound of Example 9 using the procedure of Example 8.. Yield: 340 mg (28%)

MW 450.495

Anal: (C18H18N4O6S2) Calc: C47.99, H 4.03, N 12.44 found C48.1, H 4.4, N 12.3.

EXAMPLE 11

Formulations for pharmaceutical use incorporating compounds of the present invention can be prepared in various forms and with numerous excipients. Examples of such formulations are given below.

| Tablets/Ingredients | | Per Tablet |
|---|---|---|
| 1. | Active ingredient (Cpd of Form.I) | 0.5 mg |
| 2. | Corn Starch | 20 mg |
| 3. | Alginic acid | 20 mg |
| 4. | Sodium alginate | 20 mg |
| 5. | Mg stearate | 1.3 mg |

Procedure for tablets:

Step 1 Blend ingredients No. 1, No. 2, No. 3 and No. 4 in a suitable mixer/blender.

Step 2 Add sufficient water portion-wise to the blend from Step 1 with careful mixing after each addition. Such additions of water and mixing until the mass is of a consistency to permit its converion to wet granules.

Step 3 The wet mass is converted to granules by passing it through an oscillating granulator using a No. 8 mesh (2.38 mm) screen.

Step 4 The wet granules are then dried in an oven at 140° F. (60° C.) until dry.

Step 5 The dry granules are lubricated with ingredient No. 5.

Step 6 The lubricated granules are compressed on a suitable tablet press.

Parenteral Formulation

A pharmaceutical composition for parenteral administration is prepared by dissolving an appropriate amount of a compound of Formula I in polyethylene glycol with heating. This solution is then diluted with water for injections Ph Eur. (to 100 ml). The solution is then sterilized by filtration through a 0.22 micron membrane filter and sealed in sterile containers.

What is claimed is:

1. A compound having hemoregulatory activity of the formula

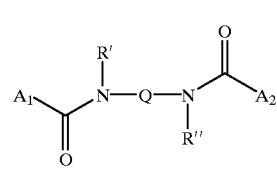

(I)

wherein:

$A_1$ equals $A_2$ and denotes a group Z, wherein Z is pyridinyl, pyrimidinyl, pyrazinyl, pyridazinyl, quinolinyl, tetrahydroquinolinyl, azetidinyl, or pyrrolidinyl wherein the ring is substituted or unsubstituted by one or two $C_{1-4}$alkyl, $C_{1-4}$alkoxy, $(CH_2)_m R_4$, oxo, oxime, O—$C_{1-4}$alkyloxime, hydroxy, amino, $C_{1-4}$alkylamino, di$C_{1-4}$alkylamino, acylamino or aminoacyl groups;

R' and R" are the same and are hydrogen, or $C_{1-4}$alkyl;

Q denotes a group

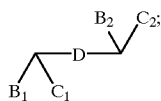

wherein:
B$_1$ equals B$_2$ and denotes —(CH$_2$)$_{m+1}$—R$^2$, —(CH$_2$)$_m$—R$^3$, or —(CH$_2$)$_m$—COR$^2$;
R$^2$ denotes —OR$^3$
R$^3$ is hydrogen, C$_1$–C$_4$-alkyl or benzyl; and
m is an integer from 0 to 4;
C$_1$ equals C$_2$ and denotes —(CH$_2$)$_{n+1}$—R$^4$ or (CH$_2$)$_n$—R$^3$;
R$^4$ is —OR$^3$;
n is an integer from 0 to 4; and
D denotes —(CH$_2$)$_x$—E—(CH$_2$)$_y$—; wherein
E denotes a single bond or —C=C—, or —C≡C—;
x and y independently denote an integer from 0 to 5; with the proviso that
x and y are not 0 if E denotes a single bond;
and with the proviso that B$_1$ is not identical to C$_1$ and B$_2$ is not identical to C$_2$, and pharmaceutically acceptable salts thereof.

2. A compound according to claim 1 wherein Z is 2-pyridinyl, 2-pyrimidinyl, 2-pyrazinyl, 2-pyrrolidon-5-yl or 2-pyrrolidinyl.

3. A compound according to claim 2 which is (R,R)-2,7-Bis-(2-pyridylcarbonylamino)-octanoic-(1,8)-diacid, (R,R)-2,7-Bis-(2-pyridylcarbonylamino)-decanoic-(1,8)-diacid, (S,S)-2,5-Bis-(2-pyridylcarbonylamino)-hexanoic-1,6-diacid, (R,R)-2,5-Bis-(2-pyridylcarbonylamino)-hexane-1,6-diol, (R,R)-2,7-Bis-((2S)-5-oxo-2-pyrrolidylcarbonylamino)-octanoic-1,8-diacid, or (R,R)-2,7-Bis-(2,pyridylcarbonylamino)-(E)-oct-4-enoic-1,8-diacid.

4. A compound according to claim 2 wherein Z is unsubstituted or substituted by methyl, ethyl, methoxy, methoxymethyl, oxo, oxime, hydroxy, amino, ethylamino or dimethylamino.

5. A compound according to claim 2 wherein R' and R" are equal and denote hydrogen, methyl, ethyl, propyl, butyl, $C_{1-4}$-alkylcarboxylic acid or $C_{2-4}$-alkylhydroxy.

6. A pharmaceutical composition comprising a compound according to claim 1 and a pharmaceutically acceptable carrier.

7. A method of stimulating the myelopoietic system which comprises administering to a subject in need thereof, an effective amount to stimulate said myelopoietic system of a compound of claim 1.

8. A method of treating viral, fungal and bacterial infections which comprises administering to a subject in need thereof, an effective amount of a compound of claim 1.

9. A method of treating sepsis which comprises administering to a subject in need thereof, an effective amount of a compound of claim 1.

10. Process for producing a compound as claimed in claim 1, said process comprising
   a) coupling two suitably protected amino acids;
   b) removing the protecting groups from the amino-functions;
   c) bis-acylating the resulting diamine with heterocyclic acids;
   d) otionally reducing and/or oxydizing any functional groups and/or removing any remaining protecting groups; and
   e) optionally forming a pharmaceutically acceptable salt thereof.

11. Process for producing a compound as claimed in claim 1, said process comprising
   a) reacting a suitably substituted 2,5-Dihydropyrazine with an appropriate dielectrophile;
   b) hydrolyzing and opening of the rings;
   c) bis-acylating the resulting diamine with heterocyclic acids;
   d) optionally reducing and/or oxydizing any functional groups and/or removing any remaining protecting groups; and
   e) optionally forming a pharmaceutically acceptable salt thereof.

* * * * *